United States Patent [19]
Stephenson

[11] Patent Number: 5,919,009
[45] Date of Patent: Jul. 6, 1999

[54] BORING SYSTEM AND METHOD

[75] Inventor: Everett H. Stephenson, Savannah, Ga.

[73] Assignee: Union Camp Corporation, Princeton, N.J.

[21] Appl. No.: 08/935,432

[22] Filed: Sep. 23, 1997

[51] Int. Cl.$^6$ .................................................. B23B 35/00
[52] U.S. Cl. ........................................ 408/1 R; 408/137
[58] Field of Search ............................... 408/92, 97, 101, 408/102, 137, 204

[56] References Cited

U.S. PATENT DOCUMENTS

| | | | |
|---|---|---|---|
| 332,274 | 12/1885 | Miller . | |
| 683,797 | 10/1901 | Reardon | 408/101 |
| 806,171 | 12/1905 | Moye | 408/92 |
| 885,943 | 4/1908 | Moore | 408/101 |
| 897,167 | 8/1908 | Sims . | |
| 1,067,672 | 7/1913 | Peterson | 408/137 |
| 1,081,552 | 12/1913 | Penn et al. | 408/92 |
| 2,707,615 | 5/1955 | Green | 254/100 |
| 2,849,900 | 9/1958 | Heidtman, Jr. | 77/14 |
| 3,110,184 | 11/1963 | Gruetzman | 73/425 |
| 3,307,435 | 3/1967 | Floren | 408/92 |
| 3,847,501 | 11/1974 | Doty | 408/101 |
| 3,967,687 | 7/1976 | Fowler | 173/32 |
| 4,094,612 | 6/1978 | Krieg | 408/92 |
| 4,487,271 | 12/1984 | Pomeroy et al. . | |
| 4,936,720 | 6/1990 | Dolatowski et al. . | |
| 4,978,257 | 12/1990 | Nowman | 408/137 |
| 5,433,121 | 7/1995 | Torra et al. . | |
| 5,433,560 | 7/1995 | Duncan . | |
| 5,651,646 | 7/1997 | Banke et al. | 408/204 |
| 5,785,466 | 7/1998 | Haynes | 408/97 |

OTHER PUBLICATIONS

Haglof Increment Borers, p. 42.
Suunto Increment Borers, p. 43.

Primary Examiner—Andrea L. Pitts
Assistant Examiner—Adesh Bhargava
Attorney, Agent, or Firm—Synnestvedt & Lechner

[57] ABSTRACT

A system and method are disclosed for drilling into an object with a drill bit. The system comprises: (a) a frame having a front and back orientation and at least one configuration, the at least one configuration being a drilling configuration; (b) a driving assembly supported by the frame during drilling, the driving assembly transferring a rotational force from to a drill bit, and, at least initially, providing a forward axial force to the drill bit; and (c) attachment means for releasably and rigidly securing the frame to the object.

21 Claims, 6 Drawing Sheets

BORING SYSTEM AND METHOD

FIELD OF INVENTION

The present invention relates generally to boring or drilling objects. More specifically, the invention relates to a system and method for high torque boring or drilling of large objects, such as trees, with long and/or large diameter drill bits.

BACKGROUND OF THE INVENTION

Many applications require drilling or boring into large objects with long, often thick, drill bits to create a bore hole or to retrieve a core sample of the object. An example of one such application is in the field of forestry where core samples are taken from trees for analysis purposes. The analysis may involve simple determinations such as tree age, growth rate, and penetration of chemicals, in which case, relatively small diameter cores are adequate, or it may entail more sophisticated evaluations such as wood anatomy, wood properties, and data collection for tree breeding programs (specific gravity, fiber length and angle, etc.), in which case, larger cores, typically 12 mm (½"), are required.

Manual tools for extracting core samples of wood are used commonly by foresters and technicians. The conventional coring tool uses a tubular bit with a tapered, external thread machined on a short, leading section of the tip, which is sharpened with a single, peripheral bevel on the exterior. Coring bits are available in various lengths. Foresters generally use somewhat longer bits than necessary to reach the center of the largest expected trees. A square section machined on the driven end of the bit engages a T-handle. The T-handle provides leverage for a user to twist the bit. After the hollow, threaded bit is twisted into the tree or wood to be sampled, the core is extracted from the drill bit typically with an extractor.

Manual coring of a tree or lumber using these tools can be an arduous task. For obtaining relatively small diameter cores, typically 5–7 mm in diameter, these tools generally can be started manually, simply by leaning into the tree, pushing on the T-handle, and twisting. Dense woods, slightly dull bits, or repetitive corings, however, test an individual's strength and endurance. Moreover, manual starting of ½" diameter core bits requires much greater force, generally exceeding the capability of a man leaning into the tool.

Manufacturers of these core tools have developed a fixture for starting them. It consists of a threaded collar which is strapped snugly to the tree with a web harness. Rotating the collar with a large T-handle forces the bit into the tree until its external male thread engages. The starting fixture is then removed, and the core bit is driven through the tree.

Although these fixtures help in starting larger bits, delivering the required torque to the bit remains a strenuous task. The torque required to core large or dense trees with a ½" bit, for example, ranges from approximately 50 to approximately 100 lb-ft. with a 2-ft. T-handle. Furthermore, it is necessary often to drill the ½" core bits completely through the tree, not just to its center. Even boring a single tree under these conditions can be tremendously fatiguing. Moreover, since there is no support or guide for these relatively thin-walled, 12 to 18" long core bits, it is easy to bend the bit, especially when "leaning" into the bit and handle to deliver the required torque. Aside from damaging the drill bit, bending the bit also causes misalignment, or, in other words, a divergence from the bit's intended path. This misalignment, for example, may cause the bit to miss the center of the tree, resulting in an unbalanced, and possibly crooked, core sample. The continuous, arduous task of coring trees using these manual drills and their limited success therefore has chilled their acceptance and widespread use.

Several attempts have been made to mechanize the collection of core samples, especially larger diameter cores, using either electrical or hydraulic power tools. These attempts, however, have been met with limited success. Heavy duty electric drills tend to rotate too fast to be safe and have insufficient torque. Suitable hydraulic tools are not commercially available, and custom-built hydraulic equipment tends to be complicated, expensive, and heavy. Since tree core samples are usually obtained in remote areas, a suitable coring device should be simple to operate, reliable and easily transported. Complicated, heavy equipment which requires care and is prone to failure is clearly not acceptable. Therefore, a need exists for a convenient boring or drilling system that can deliver high torque and initiate boring while maintaining drill bit alignment. The present invention fulfills this need among others.

SUMMARY OF INVENTION

The present invention provides a system of commercially-available or easily-fabricated components for boring or otherwise drilling an object with a relatively large and/or long bit. The system is designed to urge the bit forward into the object with a rotational motion, while delivering high torque and maintaining drill bit alignment. As used herein, the term "drill bit" refers to drill bits, augers, hole cutters, boring bits, coring bits, screws and any other substantially cylindrical device which penetrates a material through rotational motion. The term "drilling" refers to drilling, boring, coring or otherwise advancing a rotating drill bit into the object.

One aspect of the present invention is a system for drilling objects. The system basically comprises a driving assembly, a frame for supporting the driving assembly, and attachment means for securing the frame to the object to be drilled.

The driving assembly provides rotational force to the drill bit and, at least during the initial drilling phase, urges the drill bit forward. The driving assembly provides rotational force to the drill bit by acting as a coupling between the rotating means and the drill bit. It urges the drill bit forward by converting a portion of the rotational force (supplied by the rotating means) to an axial force. In a preferred embodiment, the driving assembly comprises a cylindrical member having an end adapted for receiving and rotationally engaging a drill bit, and means for releasably engaging a mechanism for rotating the drill bit. Additionally, at least a portion of the cylindrical member is threaded. The driving assembly also comprises a cooperating member which has threads adapted for interengagement with at least a portion of the cylindrical member's threaded portion. When the threads of the cylindrical member and the cooperating member are interengaged, a rotational movement of the cylindrical member (relative to the cooperating member) also results in its relative axial movement. Optionally, the driving means may also comprise rotating means, preferably an electric motor, for rotating the drill bit.

When drilling, the driving assembly is supported by a frame having a front and back orientation and at least one configuration, herein referred to as the "drilling configuration." As the name suggests, the frame is in the drilling configuration when drilling, as opposed to, for example, a "collapsed configuration" when not in use. The frame has a first support toward the front of the frame for directing the drill bit and restricting it to substantially axial movement. Additionally, the frame has a second support, which, when the frame is in its drilling configuration, is in back of the first support. The second support is adapted to receive the cooperating member and prevent it from rotating and moving axially backward during the drilling operation. Optionally, the frame may comprise also counter-rotational means for preventing the rotating means from counter-rotating during the drilling operation as high torques may be encountered.

The frame is secured to the object with attachment means. By rigidly affixing the frame to the object, the attachment means prevents the frame from moving and thereby bending the bit during high torque drilling. This rigid mounting also enables the user to drill precisely into the object.

During the initial drill phase, when the drill bit and cylindrical member are rotationally engaged, when the threads of the cooperating member and cylindrical member are interengaged, and when the cooperating member and the second support are engaged, the drill bit is held rigidly by the first support directly and by the second support through the cylindrical member. A clockwise rotation of the cylindrical member (in the case of right-handed threads) will result not only in the drill bit rotating, but also in the forward advancement of the cylindrical member (due to the screwing effect of the stationary cooperating member). The forward advancement urges the drill bit into the object. If the drill bit is threaded, the cylindrical member may be used until at least the bit "bites" the object and is able to propel itself forward without the need of the cylindrical means urging it from behind. Otherwise, the cylindrical member may be used as the source of the drill bit's forward driving force.

Another aspect of the present invention is a method for drilling an object using the above-described system. The method comprises the basic steps of: (a) mounting the frame to the tree using the attachment means; (b) engaging the drill bit with the driving assembly; (c) engaging the driving assembly and the drill bit with the frame; and (d) rotating the driving assembly. As mentioned above, it may be advantageous to remove the driving assembly if and when the bit "bites" and has progressed into the object sufficiently to establish its direction.

The system and method of the present invention provides significant advantages over the prior art. For example, it allows a user to accurately drill objects without physical exertion. The frame accurately guides and supports the bit, while the driving assembly provides the axial force necessary for starting and the rotational force necessary for drilling. The user no longer needs to "lean" into the driving means to rotate and engage the drill bit. Since leaning on the drill bit is frequently the cause of its bending and/or misalignment, the system of the present invention eliminates these problems. Indeed, these and other features and advantages of the present invention will be apparent to one skilled in the art upon review of the following description.

BRIEF DESCRIPTION OF THE DRAWINGS

The features of the present invention, which are believed to be novel, are set forth with particularity in the appended claims. The invention may best be understood by reference to the following description taken in conjunction with the accompanying drawings, wherein like reference numerals identify like elements, and wherein:

DETAILED DESCRIPTION OF THE PRESENT INVENTION

Figure 1:
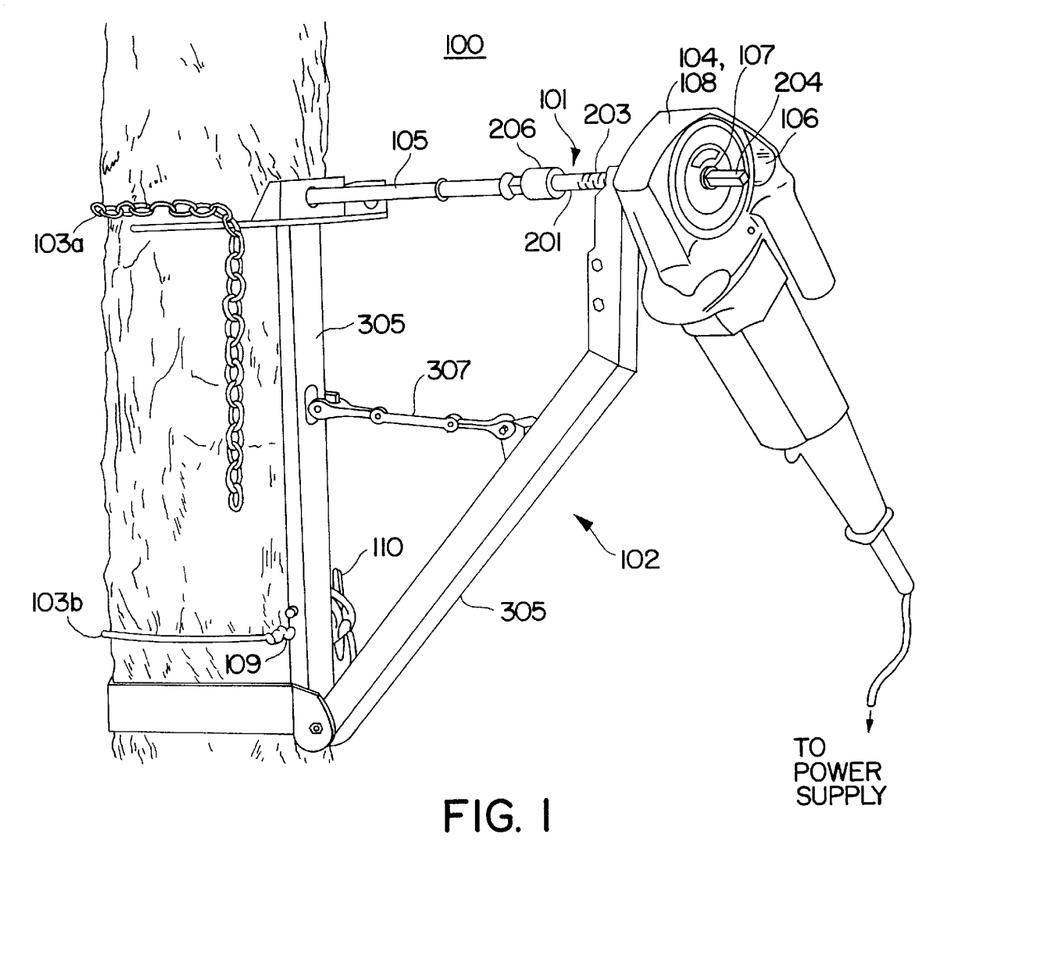
FIG. 1 shows a perspective view of a preferred embodiment of the system mounted to a tree during the initial drilling phase.

Referring to the drawings, a preferred embodiment of the present invention is depicted. FIG. 1 shows a perspective view of the system mounted on an object, in this case, a tree. It should be noted that although a tree is depicted, the system is suitable for boring other objects such as, for example, telephone poles, structural supports comprising wood, concrete, or metal, and other objects in which there is a desire to bore holes and/or obtain core samples.

As shown, the system 100 comprises a frame 102 having a front and back orientation. The frame is depicted in FIG. 1 with its front against the tree. The system also comprises a driving assembly 101 which is supported by the frame 102 during drilling. During drilling, the driving assembly 101 transfers a rotational force from the rotating means 104 to a drill bit 105, and, at least initially, provides a forward axial force to the drill bit 105. The frame is held rigidly to the object by attachment means 103. Each component of this system is discussed below in greater detail and in terms of preferred and alternative embodiments.

An important aspect of the present invention is the driving assembly which not only transfers rotational force to the drill bit, but also, at least during the initial drilling phase, urges the drill bit forward. The driving assembly provides rotational force to the drill bit by acting as a coupling between the rotating means and the drill bit. It urges the drilling bit forward by converting a portion of the rotational force (supplied by the rotating means) to an axial force. Preferably, this conversion is accomplished by a screw mechanism. In one embodiment, the driving assembly comprises an elongated, cylindrical member adapted to engage a drill bit, a cooperating member in threading engagement with the cylindrical member, and, optionally, rotating means for rotating the cylindrical member.

The cylindrical member comprises a shaft, at least a portion of which is externally threaded. One end of the shaft is adapted for receiving and rotationally engaging a drill bit. Suitable means for receiving and rotationally engaging a drill bit are well known in the art and include, for example, a socket which receives the drill bit, a chuck which is tightened about the drill bit, a male portion which interengages with a corresponding female portion of a drill bit, or any other coupling means known in the art for rotationally engaging two members. The cylindrical member also comprises means for interconnection to the rotating means. Suitable means for interconnection to rotating means are known in the art and include, for example, a nut, square shank, notch, slot and key, textured surface, or any other configuration or mechanism that provides a purchase point for rotating means.

The driving assembly also comprises a cooperating member which has threads adapted for interengagement with at least a portion of the cylinder members threaded portion. When the threads of the cylindrical member and the cooperating member are interengaged, a rotation movement of the cylindrical member relative to the cooperating member results in their relative axial movement. The cooperation means may be any surface having threads, ridges, or groves, that sufficiently interengages with the threads of the cylindrical member to resist the axial forces between the cooperating member and the cylindrical member as they rotate relative to one another. Suitable cooperating members include, for example, nuts of all shapes and sizes, a threaded trough, notch or arcuate groove, and a hinged threaded clasp that clamps around the cylindrical member. Additionally, the cooperating means may be a discrete component, such as a nut, or it may be integral to or mounted on the frame.

Figure 2:
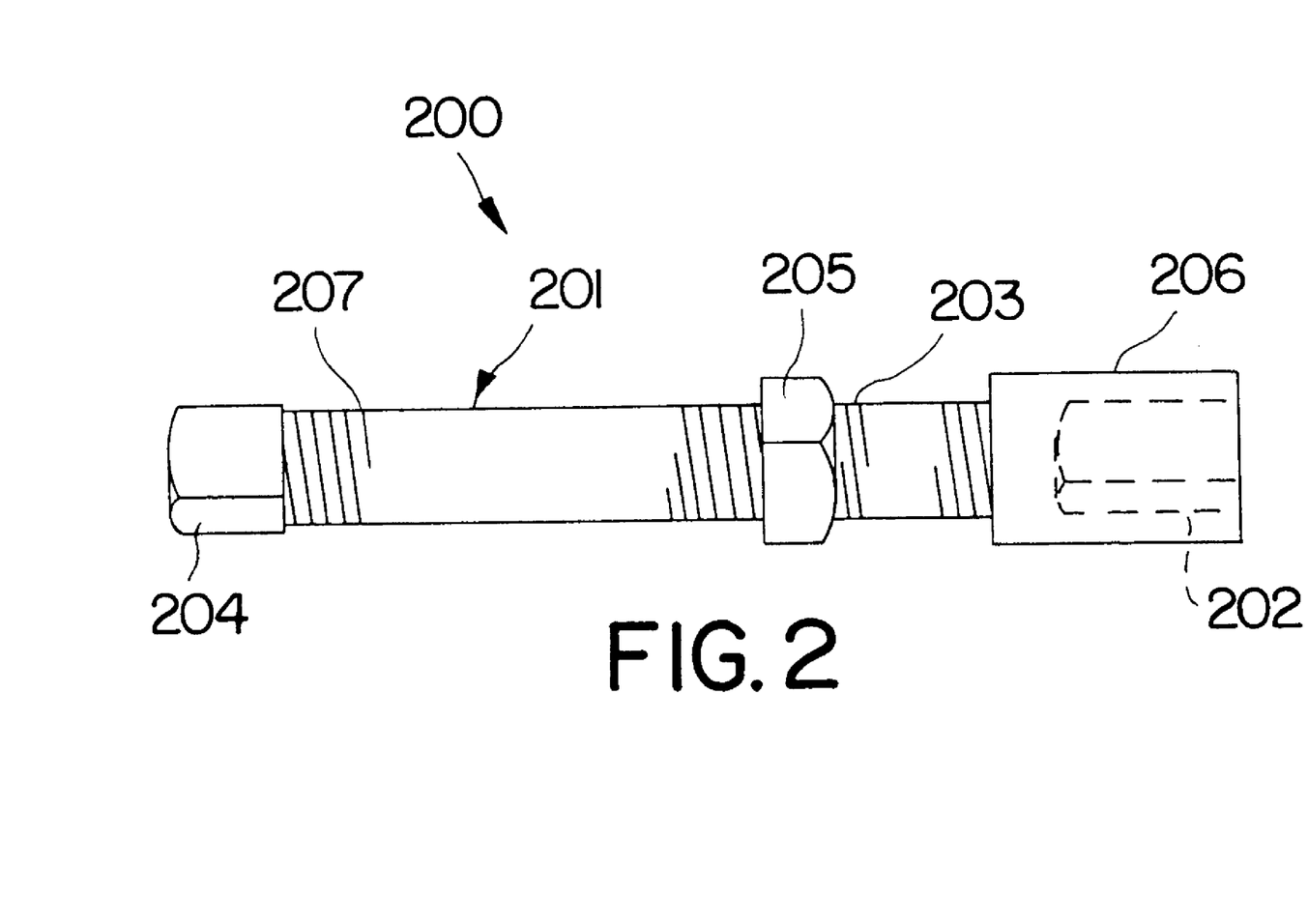
FIG. 2 shows a preferred embodiment of the driving means.

A preferred embodiment of the driving assembly 101 is shown in FIG. 2. As shown, the driving assembly 101 comprises a cylindrical member 201 having a shaft 207, a portion 203 of which is externally threaded. The means for receiving and rotationally engaging the driven end of a drill bit comprises a socket 206 which is screwed on to an end 202 of the shaft 207. The interconnection means comprises a square end 204 which is adapted to fit within an orifice 107 (FIG. 1) of the rotating means 104. The cooperating member comprises a square nut 205.

In a preferred embodiment, where the drill bit is threaded, the threaded portion 203 of the shaft 207 and the nut 205 have a higher pitch (for example, 12 threads per inch) than the drill bit (for example, 5 threads per inch). This way, once the drill bit bites the object being drilled, the drill bit will advance further per revolution than the cylindrical member. This relieves the compressive forces between the frame, cylindrical member 201 and the drill bit. Once this force is relieved, the cylindrical member may be removed, and the rotating means may be applied directly to the drill bit (discussed below).

In this embodiment, the length of the shaft 207 depends somewhat on the length of the drill bit. That is, the length of the drill bit and the shaft 207 up to the interengagement of the nut 205 should be substantially equal to the distance between supports that support the combination of the driving assembly and drill bit during drilling. Since the frame support dimensions typically are not adjustable significantly, when using a shorter bit, a longer shaft 207 may be used or the engagement region between the nut 205 and the threaded portion 203 of the shaft 207 may be moved back to effectively lengthen the drill bit/cylindrical member combination.

The rotating means of the present invention may be part of the system or supplied separately. The rotating means should be capable of delivering enough torque to the bit and/or the cylindrical member and bit combination to bore the object to the desired depth. Additionally, in many applications, it is preferable that the drill bit not rotate so fast such that it generates excessive heat which may damage the object, spoil the core sample, or damage the drill bit. In the case of forestry, the torques encountered range from about 50 ft. lb. to about 100 ft.lb., and a full load RPM of about 20 to about 30 is generally preferred. Thus, suitable rotating means should be able to provide these torques at the desired RPM. Suitable means for rotating means include, for example, electric, hydraulic and pneumatic systems and manual means having mechanical advantages such as a crank, winch, or T-handle.

Because core sampling or other drilling activity often is performed in remote areas, it is preferable that the rotating means be powered by a convenient and transportable power source. Although hydraulic units provide the power and control required, the complexity and weight of such apparatus is often times inconvenient or impractical. Therefore, in a preferred embodiment of the present invention, an electric motor is used for providing the required torque. Such a device can be conveniently powered by a portable 120V generator with ground fault protection suitable for outdoor use. The entire system, including the power supply, thus may be transported by a small all-terrain vehicle.

In the preferred embodiment, the rotating means 104 comprises a conventional, hand-held, electrically-powered, pipe threading tool 107 as shown in FIG. 1. A suitable unit is the Model 600 series pipe threading equipment offered by Rigid Tool (Elyria, Ohio). This unit has suitable speed and torque for the application, and is reversible. To releasably engage both the drill bit and the cylindrical member, it may be necessary to modify slightly the spindle of the pipe threading device. For example, the modification may entail cutting away the jaws from a ¾" pipe die head, reaming it to the outer diameter of an ¹¹⁄₁₆" eight-point impact socket, inserting the socket half its length into the die, and welding it in place. The sockets may also require minor internal enlargement with a die grinder to properly fit the metric square drive of the core bit. Such a modification, or similar modifications, however, are well within the purview of one skilled in the art.

The drill bit also may be part of the system or supplied separately. Suitable drill bits include, for example, conventional, commercially-available drills, augers or other types of boring apparatus. These bits may be threaded or non-threaded. In forestry, for example, it is common to extract core samples for analysis purposes using a hollow, threaded boring bit 106 shown in FIG. 5. Such boring bits are commercially available, for example, from Suunto and Haglof (Sweden).

The frame 102 is configured to support, guide and, during drilling, provide a backstop for the drill bit/driving assembly combination. When drilling, the driving assembly is supported by a frame having a front and back orientation and at least one configuration, the "drilling configuration." The frame not only supports the driving assembly and drill bit, but also guides it and provides a backstop against which it can urge forward. To this end, an embodiment of the frame comprises first and second supports.

The first support functions to support one end of the drill bit and to limit substantially it to front and back axial movement. Suitable support configurations include, for example, an orifice, trough, groove, clasp, bearing (roller, sleeve or ball), bushing or similar device to guide and support a drill bit. The first support preferably is made of a material softer than that of the bit such that it does not dull or in any way damage the bit. Suitable materials include, for example, wood, plastic, hard rubber, a polymeric composition, or a soft metal such as sintered bronze. In the preferred embodiment, the first support is wood due to its low cost and high configurability.

The first support may be threaded to cooperate with the drill bit or it may be non-threaded. Since drill bits may vary in thread pitch or have no threads at all, it is preferable to use a non-threaded first support. The first support should be as far forward as possible on the frame to maximize the length of the drill bit available for penetration into the object.

The frame also comprises a second support which is disposed behind the first support when the frame is in its drilling configuration. During drilling, the second support supports and the driving assembly, which is interengaged with the drill bit (the other end of the bit is supported by the first support means), and aligns the drill bit/driving assembly with the first support. The second support also, at least during the initial drilling phase, resists the backward force of the driving assembly. This involves holding the cooperating member from moving backwards or rotating as the combination of the cylindrical member and the interengaged drill bit are rotated. Suitable configurations for the second support include, for example, a notch, vice, clasp or clamp adapted to receive the cooperating member. Alternatively, the second support may be integral with the cooperating member. That is, the second support may have threads, ridges or grooves for interengaging the threads of the cylindrical member. Such a configuration may include, for example, a section of the frame having a threaded orifice.

Figure 3:
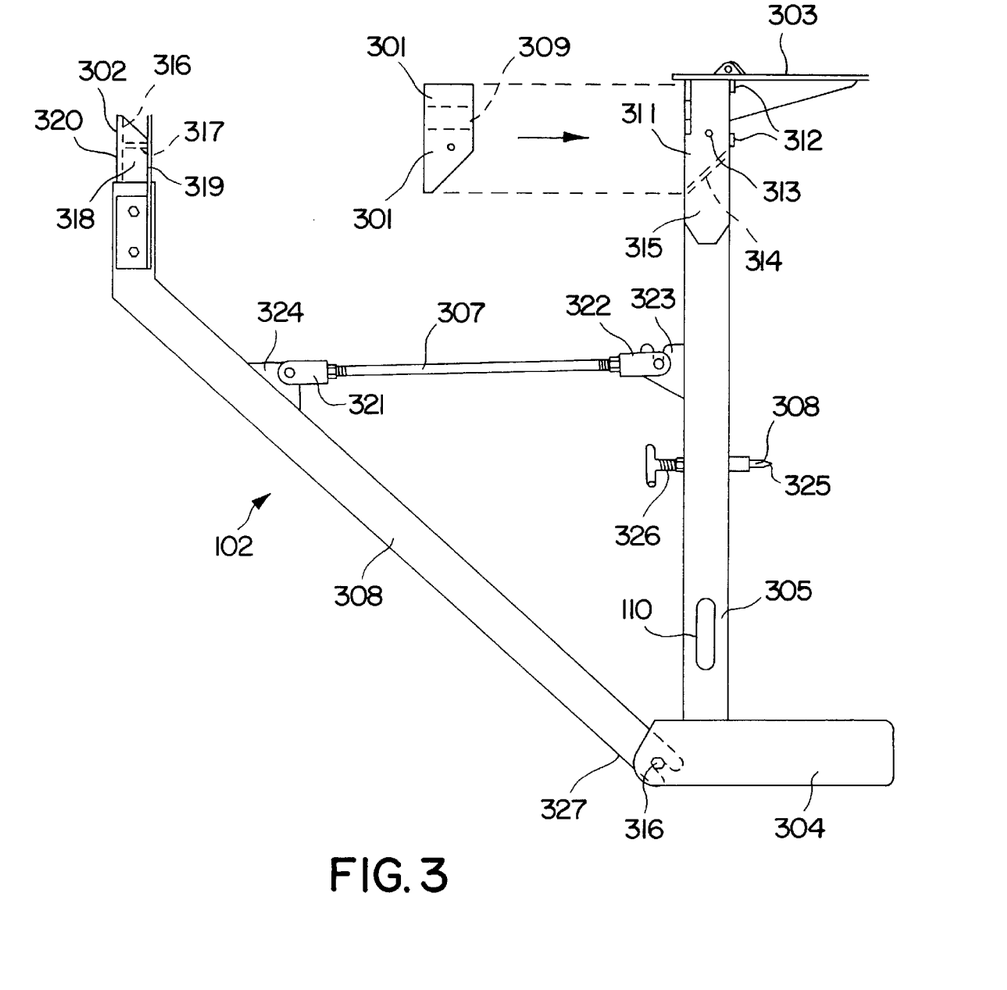
FIG. 3 shows a preferred embodiment of the frame.

A preferred embodiment of the frame in its drilling configuration is shown in FIG. 3. The frame depicted in FIG. 3 differs slightly from the one shown in FIG. 1 in that the first support 301 does not project upward from the frame 102. Rather, the first support 301 is contained with in the frame. This embodiment is preferred to avoid interference between the first support and the object being drilled when the frame is pivoted during mounting (discussed below). As shown, the first support 301 has an orifice 309 which is adapted to receive a drill bit.

Also in the preferred embodiment, the first support 301 is removable from the frame. As shown in FIG. 3, the first support 301 has a trapezoidal cross section as viewed from the side. This shape allows the first support to be removed in the event that the drill bit cannot be reversed out or otherwise be removed from the object. The significance of the shape is discussed in more detail below in regard to the process of drilling.

The preferred embodiment of the second support 302 is also shown in FIG. 3. The second support 302 has identical side plates 318 and front and rear plates 319, 320 respectively. The front and rear plates have aligning notches 316 (perpendicular to the plane of the drawing) for accommodating and supporting the cylindrical member (not shown). In this embodiment, the notches are vertical and allow the cylindrical member to be dropped into the second support 302. The notches, however, may have a diagonal or zig-zag configuration depending upon the needs of the application. A shelf 317 is provided for supporting the cooperating means, in this embodiment, a nut 205 (See FIG. 2). The side plates 318 are spaced apart such that the nut cannot rotate when seated on shelf 317. Additionally, the rear plate 320 is sufficiently strong to resist the axial force exerted by the nut as the cylindrical means is rotated. In this way, the rear plate 320 of the second support acts as a backstop for the driving assembly.

In a preferred embodiment, the first and second supports are adjustable, up and down and/or side to side. This feature allows the drill bit/driving assembly to be adjusted and "aimed" before drilling the object. Such adjustment capability may be achieved, for example, by tolerance in cavity 311 containing the first support 301, thereby accommodating limited movement of the first support 301 within the cavity. Other means of adjustment may include set screws, on one or more sides of the first support, to move the first support accordingly and/or to hold it in its adjusted position. The second support may be adjustable by altering the position of the first and second members relative to each other with, for example, a brace 307 as described below.

The frame may also comprise mounting means for mounting to the object when drilling. The mounting means can be any configuration that interfaces with the object. Thus, suitable mounting means depend somewhat on the contour of the object to be drilled. For example, if the object is relatively planar, the mounting means would be relatively planar. On the other hand, if the object is cylindrical or spherical, then the mounting means should have a concave profile.

Figure 4:
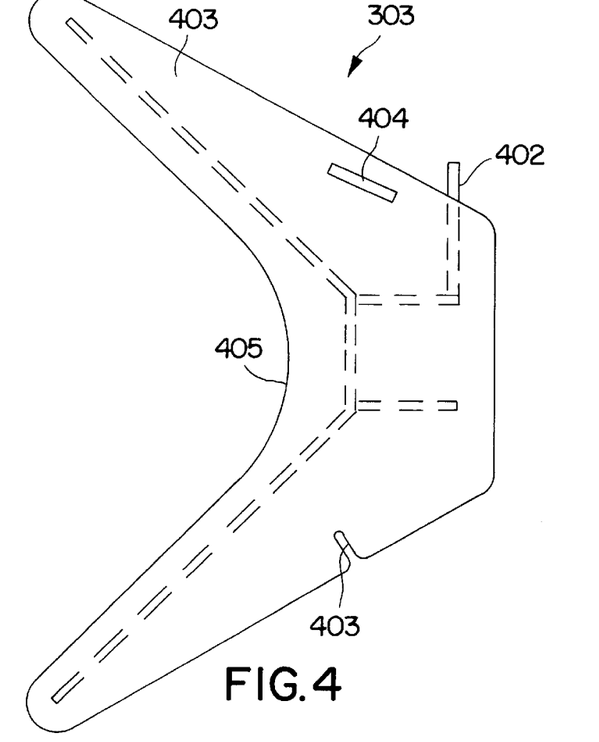
FIG. 4 shows a preferred embodiment of a first mount of the frame of FIG. 3 and the first mount's interaction with the upper attachment means.
Figure 5:
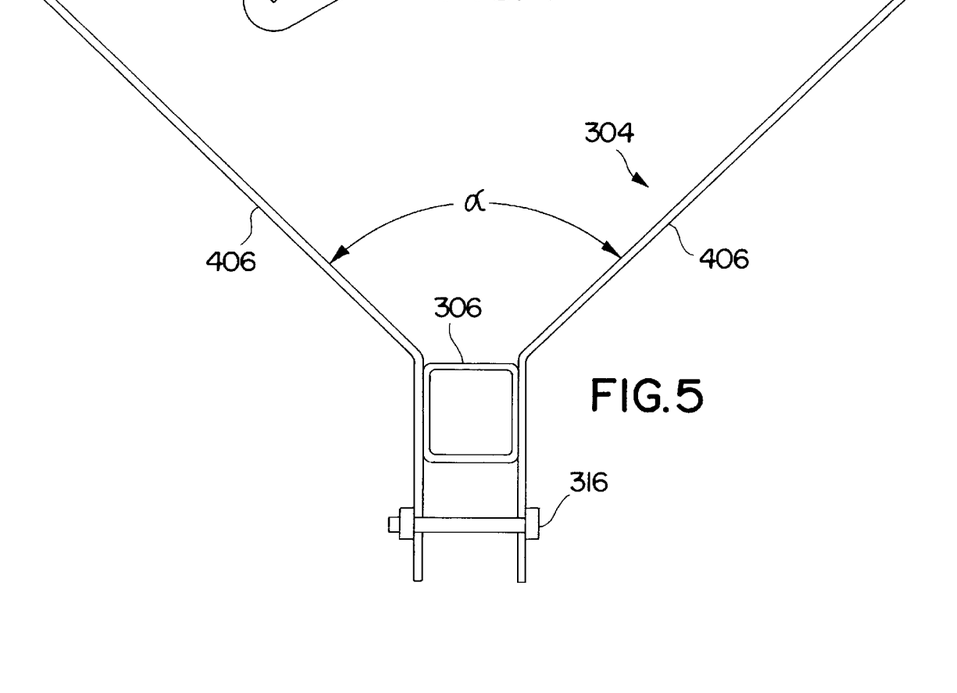
FIG. 5 shows a preferred embodiment of a second mount of the frame of FIG. 3.

FIG. 3 shows a preferred embodiment of the mounting means for mounting to a tree. As shown, the frame comprises first and second mounts 303 and 304, respectively. The first mount 303 is a plate disposed proximate to the first support 301, while the second mount 304 is a predetermined distance from the first mount 303. As shown in FIG. 4, the leading edge 405 of the plate of the first mount is concave or forked to receive a cylindrical or conical object. In FIG. 5, a preferred embodiment of the second mount is shown. Unlike the first mount, the second mount comprises to plates 406 that connected on their planar surface (perpendicular to the drawing) to the frame at an angle $\alpha$ to one another. This angle, like the concave edge of the first mount, is adapted to receive a cylindrical or conical object like a tree.

The general shape of the frame can vary providing that it supports the driving assembly and drill bit and can be rigidly secured to a tree. For example, it may have a triangular, square, or other profile; it may be casted or a structure of tubular or rectilinear sections; and it may be integral or comprised of discrete interconnecting components.

A preferred embodiment of the frame is shown in FIG. 3. In this embodiment, the frame is a structure of discrete, releasably-engaged components to provide a combination of structural strength, light weight and convenience. This design allows for not only a drilling configuration, but also a collapsed configuration for easy transportation and handling.

As shown, the frame has rectilinear first and second members 305, 306, respectively. These members may be comprised of steel tube, angle iron, or other rigid, strong material. The first and second mounts 303, 304 are disposed at proximate opposite ends of the first member 305. The second member 306 is pivotally and releasably engaged at end 327 to the second mount 304. Being pivotally and releasably connected allows the second member 306 to be angled to the first member 305 in the frame's drilling configuration, or to be dismantled or folded up closely to the first member 305 in a collapsed configuration (not shown).

When in the drilling configuration, the brace 307 extends between the first and second members 305 and 306 and holds them rigidly at an angle to one another. The brace should be designed to withstand high tension loads. Suitable braces include, for example, cable, chain, rods, and turn buckles. Preferably, the brace not only provides tension resistance, but also serves to rigidly hold members 305 and 306 together. As such, turn buckles, rods, and other stiff members are preferred. As shown in FIG. 3, the brace 307 is a rod having adjustable shackles 321 and 322. The shackle 321 pivots on a mount 324 on the second member 306 and the other shackle 322 cooperates with a notched mount 323 on first member 305 for releasable engagement.

In this preferred embodiment, the first support 301 is disposed along said first member 305 at a certain distance away from where the attachment means connects to the first member 305. More specifically, the first support 301 is below the first mount 303, which, as discussed below, is the point at which the upper attachment means connects to the frame. By spacing the upper attachment means from the first support, the chance of the drill bit exiting the far side of the object during drilling and being damaged by or damaging the attachment means is reduced.

Figure 7:
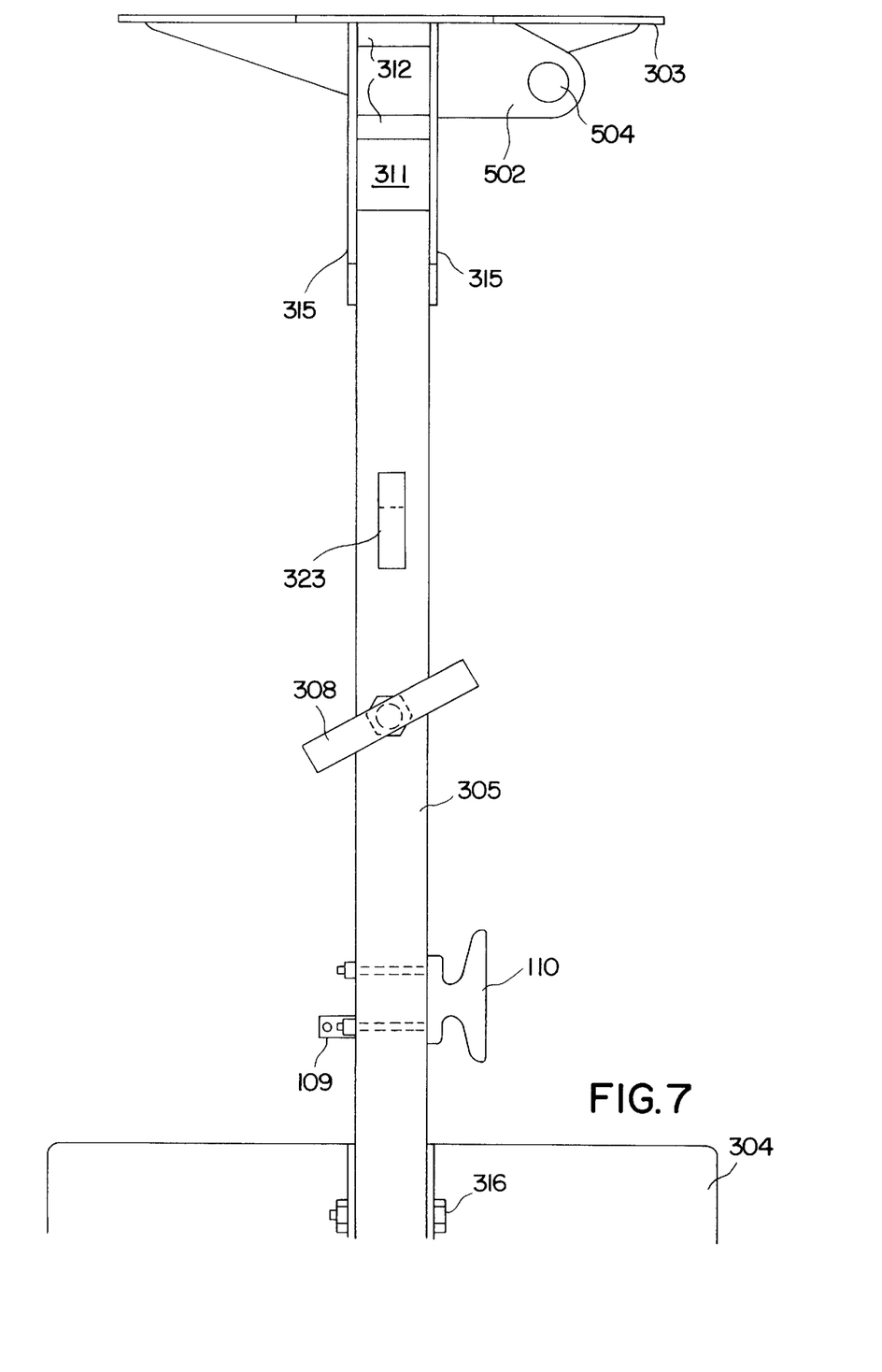
FIG. 7 shows a back view of the first member of the frame of FIG. 3.

In the preferred embodiment, as shown in FIGS. 3 and 7, a cavity 311 for the first support 301 is created by connecting the first mount 303 to the first member 305 with flat bars 315. Within this cavity, the first support is held in by two horizontal backing bars 312 and a push pin 313 with spring loaded retainer (not shown). The bottom 314 of this cavity 311 is sloped downward from front to back. This slope accommodates the drill bit when the first support 301 is removed and the frame is pivoted upwards to remove the frame when the drill bit cannot be reversed out (discussed below).

Figure 6:
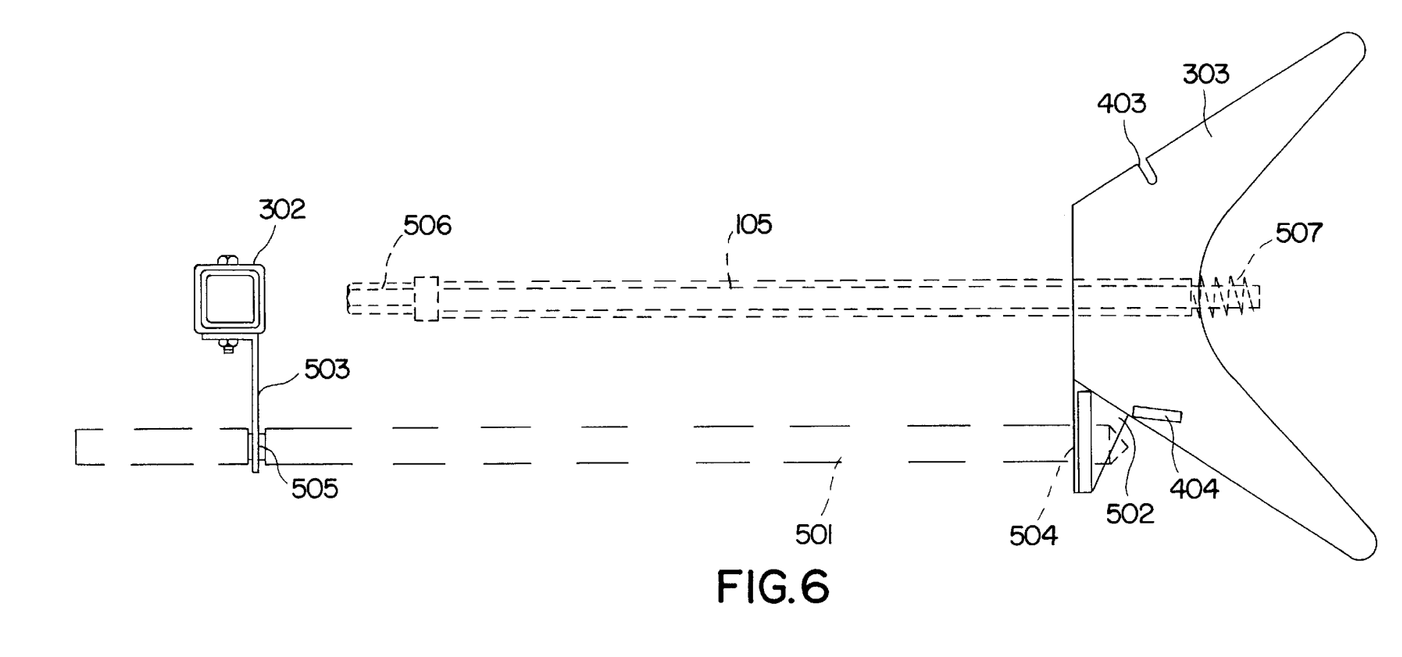
FIG. 6 shows a top perspective of a frame of FIG. 3 with the rigid rod indicated as a phantom line.

When encountering high torque, it may be beneficial to prevent the rotating means from counter-rotating by using counter-rotational means. Many variations of the counter-rotational means will be apparent to those skilled in the art. The counter-rotational means may be any mechanism which holds the rotational means from rotating relative to the frame. Suitable mechanisms include, for example, a bar, strap, hook or other such means for extending from said frame and interfering with the counter rotation of the rotating means. In the preferred embodiment, as shown in FIGS. 6 and 7, the frame has rod mounts 502 and 503 with orifices 504 and 505, respectively, for receiving a rigid rod 501. When the frame is in its drilling configuration, the rigid rod 501 extends from front to back substantially parallel to the drill bit and/or the combination of the drill bit and driving assembly. Rigid rod 501 provides a surface which the rotating means can urge against. In a more preferred embodiment in which the rotating means is a pipe threader, the rigid rod 501 has a cross sectional profile suitable for insertion through an orifice 106 of the pipe threader (see FIG. 1). This way, as the pipe threader spins the drill bit, and the drill bit advances into the object being drilled, the threading device slides axially along the rigid bar.

The frame is held rigidly to the object to be drilled by attachment means. Suitable attachment means include any conventional device or devices used to secure one object to another, such as, for example, devices that wrap around the object such as chains, straps, lines or cables as well as devices that mechanically engage the object such as spikes, screws or other type of fastener. In a preferred embodiment, two or more attachment means are employed. It is also preferred that the attachment means, particularly those that wrap around the object, tighten easily. This tightening action may be accomplished in a variety of ways, including, for example, by leveraging off the first support (described below), or by traditional tie down or tensioning mechanisms, for example, a chain fall, block and tackle, or strap lever.

The preferred embodiment shown in FIG. 1 has an upper and lower attachment means, 103a and 103b, respectively, for securing the frame to the object. The top attachment means 103a is a chain and the lower attachment means 103b is a non-stretching cord. FIG. 4 shows one preferred embodiment of the interaction between the first mount and the upper attachment means. As shown in this figure, a pad eye 404 is adapted to receive a link of chain. This chain can be wrapped around the object and brought back and secured in slot 403. As shown in FIG. 1, the lower attachment means 103b can be fastened to the frame at point 109, wrapped around the object and cleated to the frame on cleat 110.

In the embodiment of FIG. 3, the attachment means also includes a tree spike 308. It has been found that some species of trees require this feature. For example, during coring dense wood and large trees, the power tool reaction on the frame, which is principally downward, increases. At times, the frame may slip down slightly so the first support 301 is bearing on the top of the core bit. The tree spike is intended to augment the tree clamping capability and prevent slippage (a first support of anti-friction material such as ultra high molecular weight polyethylene also improves this situation). The tree spike 308 shown in FIG. 3 is a T-shaped member having a pointed end 325 and a threaded shaft 326 that cooperates with the first member 305. By rotating the T-shaped member, the tree spike 308 moves axially such that it may be screwed into the tree prior to coring. Although a T-shaped member is shown in FIG. 3, other embodiments, such as screws or nails may be used.

The operation of the above-mentioned system is straight forward and easily conducted in remote areas. In a basic embodiment, the method comprises the steps of: (a) mounting the frame to the tree using the attachment means; (b) engaging the drill bit with the driving assembly; (c) engaging the driving assembly with the frame; and (d) rotating the driving assembly. As mentioned above, it may be advantageous to remove the driving assembly if and when the bit "bites."

By way of example, the method will be described in regard to the preferred embodiment of the frame 102, shown in FIG. 3, taking a tree core sample. First, the frame 102 is rigidly fastened to the tree, with the first support 301 being positioned at the desired location for taking the core. This is done by placing the first mount 303 against the tree, tilting the first member 305 up at an angle to the tree, preferably about 45 degrees, passing the upper attachment means 103a (shown in FIG. 1 as chain) around the tree, and fastening it loosely. The lower end of the first member 305 is then pushed downward, pivoting the first member on the first mount until the second mount meets the tree. This motion tensions the upper attachment means by leveraging off the "forked" geometry of a the first mount 303 (see FIG. 4). The tipper attachment means 103a should be adjusted such that the first mount 303 bites firmly into the tree just as the second mount 304 contacts the tree. The lower attachment means 103b (shown in FIG. 1 as a cord) is then passed around the tree and cleated. These steps result in the first member 305 being rigidly mounted to the tree.

Once the first member 305 is rigidly secured to the tree, a slotted end 327 of the 30 second member 306 is positioned on the pivot pin 316, at the bottom of the frame. Next, the brace 307 is hooked between the first and second members 305 and 306. The length of the brace 307 is configured such that the first and second supports 303, 304 are aligned in regard to the desired direction of the drill bit. These steps result in the complete frame being prepared to receive the drill bit and driving assembly.

The geometry of the mounting means, particularly the forked or concaved profiles of the first and second mounts, receive the curved surface of the tree such that the driving assembly aligns with the center of the tree. The driving end 506 of the drill bit 106 (FIG. 6) is inserted in the socket 202 of the cylindrical member 201 (FIG. 2). The bit is then inserted through the first support 301, and the threaded portion 203 of the cylindrical member 201 together with the cooperating member 205 (FIG. 2) is entered into the slot 316 of the second support 302. The cooperating member 205, in this embodiment, a free-running square nut, is prevented from rotating by the side plates 318 and the shelf 317. At this point, the driving assembly is fully supported by the frame.

Before drilling, a user can sight clown the drill bit and driving assembly to check the drill bit's direction. If adjustment is necessary, then the user may move the first support and/or the second support to achieve the desired entry into the tree.

Once the user is satisfied with the aim of the drill bit, the drill bit and driving assembly are rotated freely by hand until the cylindrical member pushes the bit firmly against the tree. At this point, the driving assembly is prepared to force the core bit 105 into the tree.

The rotating means is engaged with the driving assembly, and rotation begins in a clockwise direction. For the first inch or so, the cylindrical member 201, being in threaded engagement with the cooperating means and effectively the frame, advances and crowds the bit into the tree with increasing force. Eventually, the bit "bites" or engages the tree. Since the bit threads have a coarser pitch than those of the cooperating member/cylindrical member, the drill bit begins to advance faster than the cylindrical member per turn. At some point, the cylindrical member becomes free and can be easily removed. Alternatively, a drill bit may have no threads, in which case, the driving assembly is kept in place to provide the forward urging force. The rotating means may be engaged directly to the bit if the driving assembly is removed.

To guide the drill bit and prevent the rotating means for counter-rotating, a rigid rod is secured to the frame by inserting it through orifices 504 and 505. The rotating means can than urge against the rod to prevent its counter rotation. In the preferred embodiment shown in FIG. 1, the rotating means has an orifice 106 for receiving the rigid bar. Holding the rotating power tool firmly, and using the rigid rod to control the tool's reaction, the bit may be fully drilled through the tree.

Once the drilling phase is complete, a core is extracted from the core bit. This extraction may be performed using a conventional extractor and conventional techniques. In the preferred embodiment, however, the drill bit is drilled just through the tree such that the end of the drill bit can be tapped with a block to break the core free form the tree. Once the core is severed from the tree, the core can be pushed out of the drill bit using a dowel or similar tool. After the core is extracted, the bit is backed out and removed. Alternatively, the core can be removed from the drill bit after the drill bit is removed from the tree. Once the drill bit is removed, the frame is removed in the opposite sequence from installation.

It should be noted that setting up the frame and drilling the object are two distinct steps in this process. Moreover, the rotating means and the frame are physically independent of one another. Consequently, while the rotating means is being used to drill one tree, one or more other frames may be mounted and readied for the rotating means. This improves efficiency since setting up the frame often is very time consuming.

When drilling, a hollow or soft spot may be encountered, wherein the drill bit can no longer bite, and consequently cannot be advanced or reversed. In such a situation, the first support 301 can be removed thereby allowing the frame to tilted for removal just as it was installed. In such situations, it is common for the bit to be removed by cutting the tree and splitting the core section.

It should be understood that the method described above is for illustrative purposes only and should not be used to limit the claims. For example, the system may be used to drill a variety of objects such as structural supports. Moreover, other embodiments of the system may be used in the method other than the one described herein.

What is claimed is:

1. A system for drilling into an object with a drill bit, said system comprising:
   a frame having a front and back orientation and being positionable in at least a drilling configuration; and
   a driving assembly removably mountable to said frame, said driving assembly comprising a screw mechanism adapted to convert a portion of rotational force for driving a drill bit to forward axial force and to transfer said forward axial force to the drill bit; and
   attachment means for releasably and rigidly securing said frame to said object.

2. A system for drilling into an object with a drill bit, said system comprising:
   a frame having a front and back orientation and being positionable in at least a drilling configuration;
   a driving assembly supported by said frame during drilling, said driving transferring a rotational force to a drill bit, and, at least initially, providing a forward axial force to the drill bit;
   attachment means for releasably and rigidly securing said frame to said object; and
   wherein said drive assembly further comprises:
      a cylindrical member having an end adapted for receiving and rotationally engaging the drill bit and having a predetermined length at least a portion of which is threaded, said cylindrical member being adapted to releasably engaging rotating means for rotating said drill bit; and
      a cooperating member having threads adapted for engagement with at least a portion of said cylindrical member's threaded portion; and
   wherein said frame comprises at least:
      a first support toward said front of said frame for guiding said drill bit;
      a second support in back of said first support when said frame is in said drilling configuration, said second support preventing rotational and backward axial movement of said cooperating member when drilling.

3. The system of claim 2, further comprising:
   counter-rotational means operatively connected to said frame for preventing said rotating means from counter-rotating during drilling.

4. The system of claim 2, wherein the threads of said cylindrical starting member have a higher pitch than those of the drill bit.

5. The system of claim 2, further comprising:
   rotating means for rotating said drill bit, said rotating means adapted for releasable engagement with said cylindrical member.

6. The system of claim 5, wherein said rotating means is driven by an electric motor.

7. The system of claim 6, wherein said rotating means is a pipe threader adapted for releasable engagement with said cylindrical member and said drill bit.

8. The system of claim 7, wherein said frame comprises a first member, a second member, a brace, a first mount and a second mount, said first mounts being disposed at opposite ends of said first member, said second member being pivotally connected to said second mount when said frame is in said drilling configuration, said brace extending between said first and second member, said brace holding said first and second members in an angular relationship when said frame is in said drilling configuration, said first support being disposed on said first member proximate to said first mount, said second support being disposed on said second member.

9. The system of claim 2, further comprising:
a drill bit.

10. The system of claim 2, wherein said first support is removable from said frame.

11. The system of claim 2, wherein said first support is adjustable.

12. The system of claim 11, wherein said second support is adjustable.

13. A method of drilling an object comprising:
mounting a frame on said object, said frame being adapted for positioning a drill bit against said object;
positioning a drill bit on said frame against said object;
mounting a driving assembly for rotating said drill bit on said frame, said driving assembly comprising a screw mechanism adapted to convert a portion of a source of rotational force provided to said driving assembly to rotate said drill bit to forward axial force and transfer said forward axial force to said drill bit;
supplying a source of rotational force to said driving assembly to rotate said drill bit and to provide forward axial force thereto through said screw mechanism;
interrupting said supply of rotational force and removing said screw mechanism after said drill bit engages said object; and
resuming the supply of rotational force to said drill bit.

14. The method of claim 13, wherein said system comprises counter-rotational means operatively connected to said frame for preventing said rotational means from rotating during drilling, said method further comprising:
(e) preventing said rotating means from rotating using said counter-rotational means.

15. The method of claim 13, wherein said method further comprising:
sighting down said drill bit to check direction of said drill bit; and
adjusting the entry of said drill bit.

16. The method of claim 15, further comprising:
(e) extracting a core sample from within said drill bit.

17. The method of claim 13, wherein said object is a tree.

18. A system for drilling into an object with a drill bit, said system comprising:
a frame having a front and back orientation and being positionable in at least a drilling configuration;
fastener for releasably and rigidly securing said frame to said object; and
a driving assembly removably mountable to said frame, said driving assembly comprising a screw mechanism adapted to convert a portion rotational force for driving a drill bit to forward axial force and to transfer said forward axial force to the drill bit, said driving assembly being configured to allow for independent forward axial motion of the drill bit during drilling.

19. The system of claim 18, wherein said drive assembly comprises:
an cylindrical member having an end adapted for transferring said forward axial force to a drill bit and having a predetermined length at least a portion of which is threaded, said cylindrical member being adapted for releasably engaging rotating drive for rotating said drill bit; and
a cooperating member having threads adapted for engagement with at least a portion of said cylindrical's threaded portion; and
wherein said frame comprises at least:
a first support toward said front of said frame for guiding a drill bit;
a second support in back of said first support when said frame is in said drilling configuration, said second support preventing rotational and backward axial movement of said cooperating member when drilling.

20. The system of claim 19, further comprising:
a torsional-resistance mechanism operatively connected to said frame for preventing a rotating drive from counter-rotating during drilling.

21. The system of claim 19, further comprising:
a rotating drive for supplying said rotational force, said rotating drive adapted for releasable engagement with said elongated member.

* * * * *